NORWAY MAPLE TREE

Filed April 26, 1968 2 Sheets-Sheet 1

Edward H. Scanlon
INVENTOR
By Ely & Gobrick
ATT'YS.

United States Patent Office

Plant Pat. 2,973
Patented June 23, 1970

2,973

NORWAY MAPLE TREE

Edward H. Scanlon, 7621 Lewis Road,
Olmsted Falls, Ohio 44138

Filed Apr. 26, 1968, Ser. No. 724,645
Int. Cl. A01h 5/12
U.S. Cl. Plt.—51 1 Claim

ABSTRACT OF THE DISCLOSURE

A new and distinct variety of Norway maple tree (*Acer platanoides*) having an equally restricted uniform growth in lateral branch length in substantially the entire crown, generally equal spacing of lateral branches on the trunk and in turn on the structural branches, dense peripheral growth of twigs and foliage, and a resultant globular crown whereby it is primarily distinguished from the species and known varieties. The variety assumes its characterizing shape more rapidly, and has a better resistance to sunburning of the foliage, than known varieties.

Figure 1:
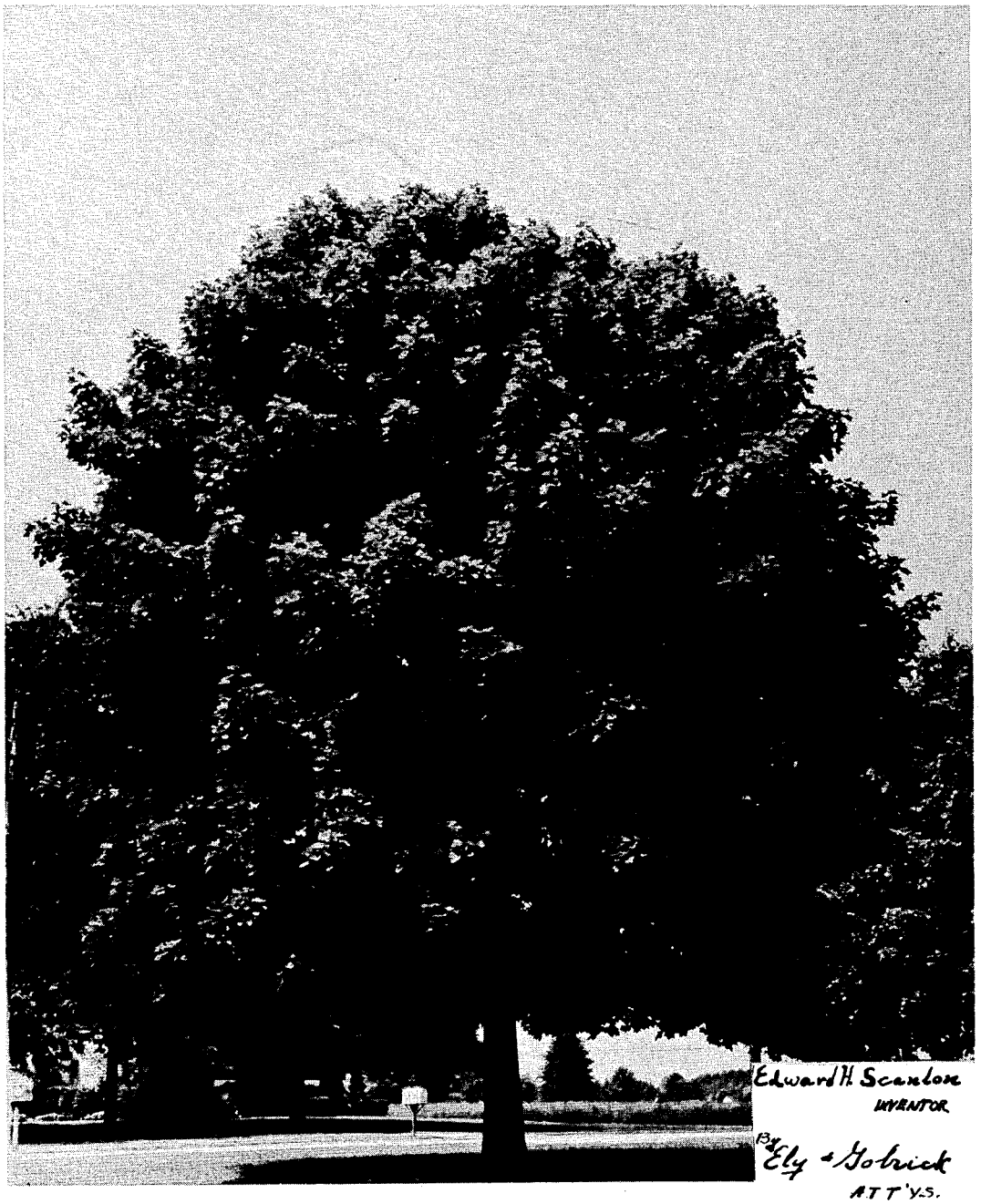
Figure 2:
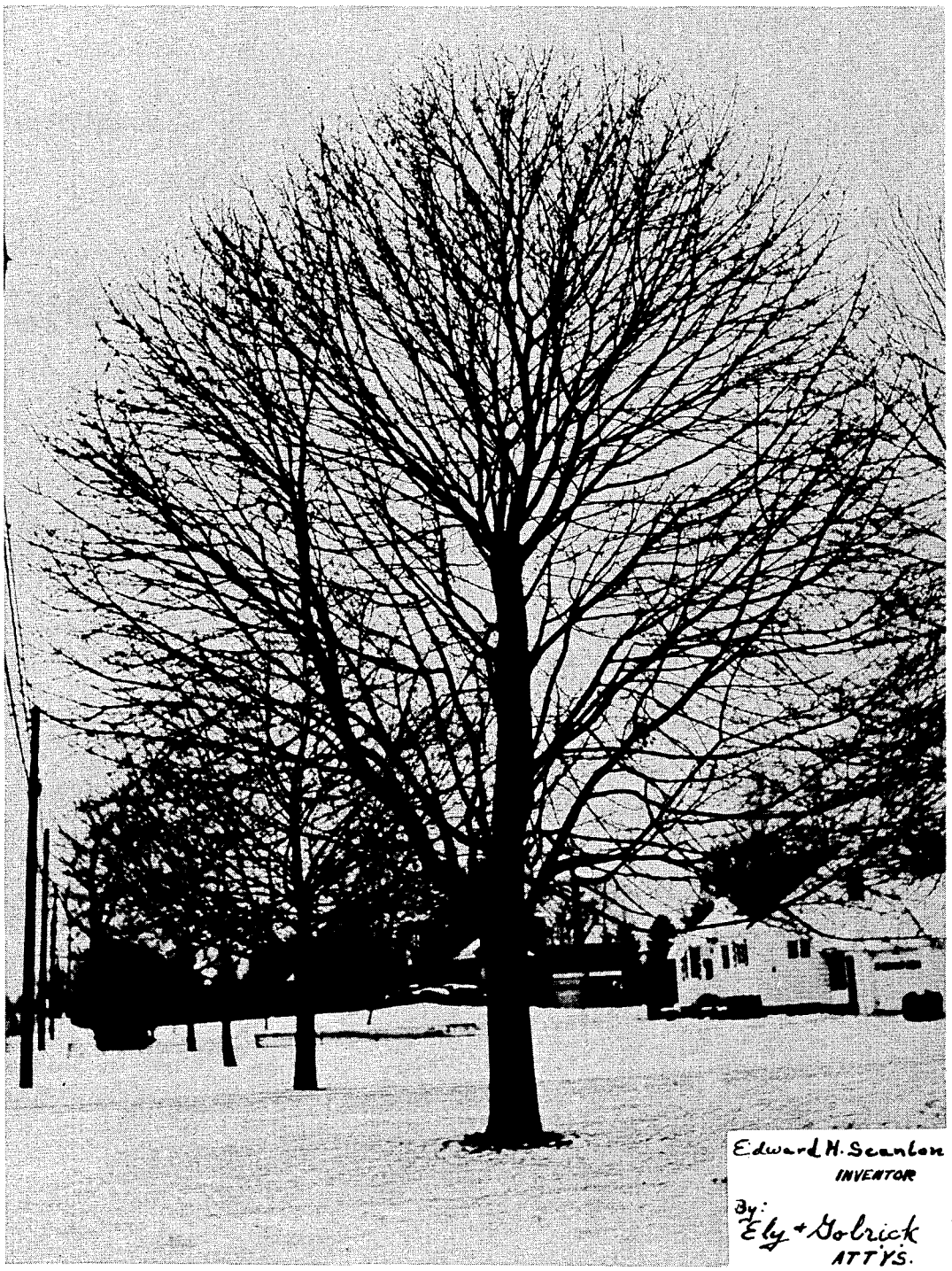

In the drawings:

FIG. 1 represents a tree of this new variety in full foliage to show its characteristic and distinguishing shape; and FIG. 2 represents the same tree in dormant state to show the more clearly its branching habit and the peripheral twig growth from which the shape derives.

This variety originated through applicant's discovery of the parent tree, a cultivated seedling distinctive in its shape among an ornamental roadside planting of Norway maples, in Olmsted Township, Ohio, and the observation of five generations of its asexually reproduced propagules.

The tree has been propagated from bud-wood supplied by applicant and at applicant's direction by budding onto *Acer platanoides* understock, near Portland, Oreg., and the hereinafter described distinguishing characteristics have been found to persist through five generations of propagules.

Branchlets: Smooth.

Leaves:

*Shape.*—Five-lobed and acuminate as in the species.

*Size.*—Quie uniform in size, consistently from 5 inches to 6 inches wide, and 5 to 6 inches long being more uniform and on the whole smaller than species.

*Color and surface.*—Very dark green and glabrous above; smooth and somewhat silvery green on underside.

Growth rate: Uniform and rapid, assuming a definite shape more rapidly than species generally; the characteristic form becoming apparent even in trees two years old.

Flowers: Generally as typical of the species.

Fruit: Generally as in the species; but noticeably smaller. This new variety appears to be not as heavy a seeder as most seeding Norway maple trees.

This new variety is a mutation primarily distinguished from any known varieties of the species by showing a prominent, rather straight central stem carried about half-way into the crown, breaking up into branches flaring out from the stem termination, and further showing an equal degree of restricted and uniform growth in the lateral branch length of the whole crown, with each lateral branch flaring out uniformly equidistant on each main and structural branch giving a compact dense outer periphery of fine twigs and foliage that result in a globular crown quite distinct from the species. Though the flower color is that of the species, this dense growth emphasizes that color and confers a striking appearance on the tree when in flower.

The new variety further appears to be superior to other known varieties in its resistance to sunburning of the foliage.

I claim:

1. A new and distinct variety of Norway maple tree as described and illustrated.

No references cited.

ROBERT E. BAGWILL, Primary Examiner